(12) United States Patent
Oaks et al.

(10) Patent No.: US 6,277,379 B1
(45) Date of Patent: Aug. 21, 2001

(54) USE OF PURIFIED INVAPLEX FROM GRAM NEGATIVE BACTERIA AS A VACCINE

(75) Inventors: Edwin V. Oaks, Gambrills; Kevin Ross Turbyfill, Waldorf; Antoinette Berrong Hartman, Silver Spring, all of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/407,330

(22) Filed: Sep. 29, 1999

Related U.S. Application Data

(60) Provisional application No. 60/102,397, filed on Sep. 30, 1998, now abandoned, provisional application No. 60/102,398, filed on Sep. 30, 1998, now abandoned, and provisional application No. 60/136,190, filed on May 27, 1999, now abandoned.

(51) Int. Cl.[7] .................................................. A61K 39/385

(52) U.S. Cl. .................................. 424/197.11; 424/193.1; 424/234.1; 424/203.1; 424/249.1; 424/241.1; 424/258.1; 424/252.1; 530/350; 435/975; 536/123.1

(58) Field of Search ............................. 424/193.1, 234.1, 424/258.1, 249.1, 241.1, 252.1, 203.1, 197.11; 530/350; 536/123.1; 435/975

(56) References Cited

U.S. PATENT DOCUMENTS 4,281,061 * 7/1981 Zuk et al. .

OTHER PUBLICATIONS

Oaks et al. Infect. Immun. 53: 57–63, 1986.*

* cited by examiner

Primary Examiner—Jennifer E. Graser
(74) Attorney, Agent, or Firm—Elizabeth Arwine; Charles H. Harris

(57) ABSTRACT

A novel composition comprising Invaplex from gram-negative bacteria is described and is effective as a vaccine against gram-negative bacterial infection.

9 Claims, 4 Drawing Sheets

Figure 1. Preparation of Invaplex 24 and Invaplex 50 from *Shigella* spp.

USE OF PURIFIED INVAPLEX FROM GRAM NEGATIVE BACTERIA AS A VACCINE

The present patent application claims priority under 35 U.S.C., Section 19(e), to the following U.S. provisional patent applications: U.S. Ser. No. 60/102,397, now abandoned, filed Sep. 30, 1998, U.S. Ser. No. 60/102,398, filed Sep. 30, 1998, now abandoned, and U.S. Ser. No. 60/136,190, filed May 27, 1999, now abandoned.

FIELD OF THE INVENTION

This invention provides a novel composition, Invaplex, comprising at least one invasin protein i.e. proteins essential for the process by which a bacterium enters a host cell, and lipopolysaccharide from invasive gram-negative bacteria. The composition of the present invention can be used as an adjuvant for vaccines, biochemical, or other substances, as a diagnostic tool, and as a vaccine against gram-negative bacterial infection.

INTRODUCTION

Bacillary dysentery is caused by members of the genus Shigella as well as enteroinvasive *Escherichia coli* (EIEC). Shigellosis is found in all parts of the world with developing countries accounting for the large majority of cases. A recent report in the Bulletin of the World Health Organization estimates that in developing countries, for children 0–4 years old, there were 113 million Shigella episodes per year and an additional 50 million cases per year in all other age groups. In industrialized countries it is estimated that there are approximately 1.5 million cases of shigellosis per year (Kotloff et al 1999, *WHO* 77, 651–666). The rampant occurance of antibiotic resistance in Shigella spp. and the high incidence of this disease underscores the need for a vaccine against this human pathogen. However at the present time a vaccine is not commercially available for bacillary dysentery.

The pathogenesis of Shigella is attributed to this organism's ability to invade, reside, and replicate intracellularly within the colonic epithelium. The invasion of host cells by Shigella spp. is a complex multifactorial event in which many different bacterial proteins are involved. Many of the genes for key Shigella virulence proteins are encoded on a large 140 Mdal plasmid. Several of the plasmid encoded proteins called the invasion plasmid antigens (IpaA, IpaB, IpaC, and IpaD proteins) (Buysse et al., 1987, *J. Bacteriol.* 169, 2561–2569) are essential virulence factors. Similar proteins, called Sip proteins, are made by members of the genus Salmonella (Kaniga et al, 1995, *J. Bacteriol.* 95, 3965–3971). Upon contact or attachment to host cells, the Shigella invasins induce a phagocytic event which results in engulfment and internalization of the bacterium by the host cell. Recent reports have identified that IpaB and IpaC form a complex that can be found in the growth medium of Shigella cultures (Menard et al, 1998, *EMBO J* 13, 5293–5302; Watari et al 1995, *EMBO J* 14, 2461–2470). The components of this complex are involved in the invasion process, but the actual mechanisms have not been defined (Menard et al, 1994, *Cell* 79:515–525). In addition, purified IpaC has been shown to bind to host cells and participate in the uptake of avirulent shigellae by host cells (Marquart et al., *Infect Immun.* 64:4182–4187, 1996). IpaB, IpaC and IpaD, along with LPS are known major antigens that infected individuals respond to after infection with shigellae (Li et al. 1993, *Scand. J. Infect. Dis.* 25, 569–577; Oaks et al, 1986, *Infect. Immun.* 53, 57–63; van DeVerg et al 1992, *J. Infect. Dis.* 166, 158–161). Monkeys or humans infected with shigellae produce antibodies predominantly to IpaB and IpaC, and also produce antibodies at high frequencey to IpaA, IpaD and VirG (another plasmid encoded virulence protein involved in intercellular spreading) (Oaks et al, 1986, supra). It is not known if the immune response to the Shigella invasins or more specifically to the invasin complex is crucial to protective immunity.

There are no proven safe and effective vaccine for shigellosis, EIEC diarrhea or salmonellosis, although several living attenuated shigella vaccines are in human trials. Unfortunately, with the many serotypes of Shigella, and because immunity appears to be serotype specific, it would require a multitude of living vaccines to cover the spectrum of serotypes in nature. In addition, living attenuated vaccines are difficult to standardize.

Therefore, there is a need for a standardized vaccine against gram-negative bacteria which can be prepared from different serotypes of Shigella without the need for attenuation of each serotype.

SUMMARY

The present invention fulfills the needs described above. In this application is described a novel composition comprising at least one invasion protein, proteins essential for bacterial invasion of a host cell. The invasion protein(s) of the present invention are complexed with lipopolysaccharide (LPS). The complex of invasin protein(s) and LPS is in a native conformation and has been termed Invaplex. The Invaplex described below is not only effective as a vaccine against gram-negative bacterial infection but it can also serve as a mucosal adjuvant and a diagnostic tool for detecting antibody responses which correlates with protection against future infection.

Our initial experiments were aimed at isolating and purifying IpaC from a water extract of Shigella, a gram-negative bacteria. Usually, IpaC is extracted from growth culture medium. We chose to use the water extract, i.e. the solution resulting from incubating the bacteria with shaking in sterile water, because we hypothesized that the quantity of IpaC would be greater in such an extract. To our knowledge, no protein involved in the invasiveness of gram negative bacteris has been previously isolated from a water extract of gram-negative bacteria. To our suprise, when water extract was subjected to various separation techniques such as gel filtration and ion-exchange chromatography, we found that whenever we could detect detect IpaC from the water extract we also detected IpaB, IpaD and LPS in the same fractions. We proceeded to design a method to isolate this complex and characterize it. We have developed a method for purifying the invasin complex from intact invasive shigellae or enteroinvasive *E. coli* (see FIG. 1 for general overview). Briefly, the Invaplex preparations are isolated from virulent, invasive shigellae. A crude mixture is extracted from the shigellae with water. The water extract consists of many proteins and lipopolysaccharide (LPS). The water extract material is then applied to a FPLC ion-exchange column which resolves two key protein peaks, called Invaplex (invasin complex) 24 and Invaplex 50. Fractions containing Invaplex 24 and Invaplex 50 are collected. We found that the complex was composed of many proteins, including IpaB, IpaC, IpaD in addition to LPS. The Invaplex 24 and Invaplex 50 preparations containing Ipa proteins and the LPS form a structure in a completely native configuration and environment.

If such a structure is used to immunize animals, it will lead to an immune response directed against a native structure presented by gram-negative bacteria during infection. Mice and guinea pigs immunized with the Invaplex preparations showed a marked serum IgA and IgG response to several different antigens (including the water extract antigen, IpaC and LPS) present in the Invaplex 24 and Invaplex 50 preparations. The two Invaplex preparations were similar in that they both primed the mucosal immune system, but differed in the specificity of the immune response generated. The animals were protected from challenge with gram-negative bacteria and immunization with either Invaplex. Animals immunized with either Invaplex showed no visible signs of distress or toxicity.

Therefore, the present invention relates to a purified composition, Invaplex, comprising invasin proteins in combination with LPS associated together to form a native structure. The Invaplex can be isolated from any invasive gram-negative bacteria such as Shigella, Salmonella or EIEC of different serotypes and combined to produce an effective vaccine against gram-negative bacteria.

Therefore, it is an object of the present invention to provide a vaccine against gram-negative bacteria comprising Invaplex from gram-negative bacteria in an amount effective to elicit protective antibodies in a subject to said bacteria; and a pharmaceutically acceptable diluent, carrier, or excipient.

It is another object of the present invention to provide a Shigella vaccine comprising Invaplex from Shigella in an amount effective to elicit protective antibodies in a subject to Shigella; and a pharmaceutically acceptable diluent, carrier, or excipient.

It is another object of the present invention to provide a EIEC vaccine comprising Invaplex from EIEC in an amount effective to elicit protective antibodies in a subject to EIEC; and a pharmaceutically acceptable diluent, carrier, or excipient.

It is another object of the present invention to provide a method of preparing a vaccine against gram-negative bacteria comprising isolating Invaplex from gram-negative bacteria.

Further objects and advantages of the present invention will be clear from the description that follows.

DETAILED DESCRIPTION

Figure 1:
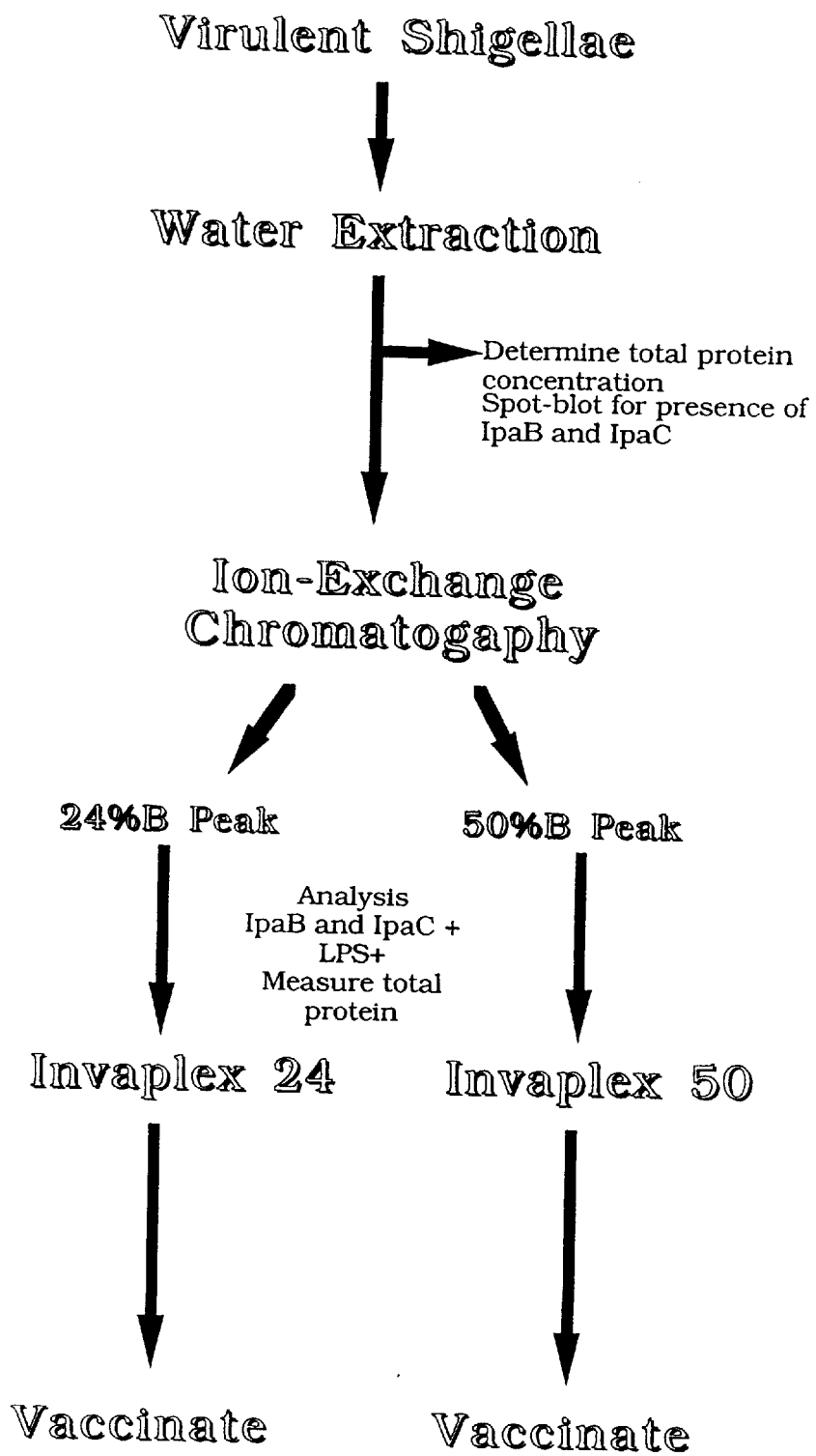
FIG. 1. Preparation of Invaplex 24 and Invaplex 50 from Shigella spp.

The present invention relates to a vaccine for gram-negative bacteria based on Invaplex and to methods for preparing such a vaccine.

More particularly, the vaccine for gram-negative bacteria described in this invention results in an improved functional (bactericidal, neutralizing, opsonizing) antibody response to gram-negative bacteria in animals and is expected to give an improved antibody response in humans, by presenting the Invasins and LPS in their natural environment as native structures. Vaccination with gram-negative subunit vaccines containing both invasins and LPS has not been effective previous to this invention. Intranasal vaccination using the present invention is expected to be an effective route of vaccination because it will induce secretory antibodies at the mucosal surface in addition to inducing antibodies in the serum. This type of vaccine will be simple and inexpensive to manufacture; allows combinations of Invaplexes from different serotypes to be combined to provide protection against more than one serotype of gram-negative bacteria, is safe and does not induce negative side effects, and dosages can be quantitated and standardized.

The Invaplex can be prepared from any gram-negative bacteria including but not limited to those classified under the following genera, Shigella, Escherichia, Salmonella, Yersinia, Rickettsia, Brucella, Erhlichiae, Edwardsiella, Campylobacter, Legionella and Neisseria. These are all invasive bacteria that have a gram-negative architecture (i.e. they have an inner or cytoplasmic membrane and an outer membrane surrounding the inner membrane).

In addition to wild type virulent gram-negative bacteria, mutants of these organisms may be useful, such as those which hyper-express quantities of invasin proteins and which might lead to the production of more Invaplex. The gene virF, for example is involved in the regulation of Ipa proteins in shigellae (Sakai et al. 1988, *Mol. Microbiol.* 2, 589–597). All documents cited herein supra and infra are hereby incorporated in their entirety by reference thereto. Furthermore, it may be beneficial to prepare Invaplex from bacteria mutated in toxin genes so that the organism does not produce toxin, for example Shiga toxin. Invaplex prepared from tox- strains would be potentially safer because potential contamination by the toxin would be eliminated.

Increased levels of Invaplex may be achieved by extracting the complex in the presence of chemicals that stimulate secretion of the invasin proteins. Such chemicals include Congo Red, Evans Blue and direct orange (Bahrani, F. K, *Infect Immun* 65:4005–4010, 1997). These chemicals could be added during the water extraction or during the growth of the bacteria.

In order to isolate the invasin proteins (Ipa proteins for Shigella or similar proteins in other invasive bacteria), the invasin proteins must be expressed by the bacteria. If the invasin proteins are not expressed on the surface or not expressed at all, the Invaplex will not be present. For example, in *S. sonnei* one must use form I cultures because they are virulent. Form II cultures do not express the Ipa proteins due to a large spontaneous deletion in the virulence plasmid. In addition, Invaplex may be isolated from bacteria to which genes encoding invasin proteins are added and expressed. Such bacteria may or may not previously contain and express invasin proteins and are chosen for a particular purpose such as ease of purification of Invaplex, or advantageous properties such as reduced toxin production.

Ipa protein presentation on the surface of shigellae may be decreased by mutating genes in the spa or mxi gene loci. The spa/mxi gene mutants make the Ipa proteins in normal quantities but the Ipa proteins are not presented or secreted to the exterior of the organism. Previously it has been shown that reduced amounts of IpaB and IpaC are in the water extract in spa mutants (Venkatesan et al., 1992, *J. Bacteriol.* 174, 1990–2001).

To overcome the possibility of using avirulent cultures, it is important that cultures used as a source of Invaplex be tested and proven to be virulent. This is usually done by the Sereny test (keratoconjunctivitis in guinea pigs as described in the Materials and Methods and Examples below). Another means in which to assure virulence is growing cultures of shigellae on Congo Red media in which colonies that are red (or bind the dye congo red) are almost always virulent. Assessment of virulence is extremely important with shigellae cultures as spontaneous mutations leading to avirulent cultures is commonplace. It is understood that even though some cultures may be partially virulent, it is possible to isolate Invaplex though the yield will be compromised.

In one embodiment, this invention relates to a method for isolating and purifying the Invaplex from gram-negative bacteria. The present method uses an improvement of the water extraction technique described by Oaks et al., 1986 (*Infect Immun* 53, 57–63). These improvements were designed to increase yield of functional product by minimizing the time to prepare the water extract preparation. The improvements include using an ion-exchange column capable of concentrating the Invaplex thereby eliminating the need to concentrate the water extract by time-consuming ultrafiltration step prior to loading onto the ion-exchange column. Ultrafiltration often took overnight to perform during which time proteolytic degradation might occur. The Ipa proteins are extremely labile and degrade rather quickly. Another improvement is the amount of water used to extract the proteins. The present method uses a volume of water which is 1/20 the volume of the medium used to grow the culture instead of a ratio of 1/10 used previously (Oaks et al., 1986, supra). For example if the shigellae are grown in 20 liters of medium than one would use 1 liter of water for the extraction. Other modifications include filtration of the water extract with a 0.45 or 0.22 um membrane both before and/or after ultracentifugation. This step will remove bacteria from the water extract material and make it less likely to contain viable bacteria. his step will be essential for any product to be used in human trials. Also the original procedure described in Oaks, 1986 (supra) used PMSF (phenylmethylsulfonyl fluroide) a very potent and dangerous protease inhibitor. This protease inhibitor is no longer used because it is toxic. To minimize degradation of the proteins in the complex the water extract is maintained on ice to minimize proteolytic degradation.

The present method includes the steps of collecting bacterial cells, extracting the cells in sterile water, separating and discarding membrane fragments from the water extract resulting in a solution containing the Invaplex, and isolating the Invaplex from the solution. Growing gram-negative bacteria in culture is known to a person with ordinary skill in the art. For a general reference, please see *Manual of Methods for General Bacteriology,* 1981, Washington, D.C., P. Gephardt et al., eds. Media and conditions for growth are discussed for Shigella in detail in Materials and Methods below. After growth, the bacterial cells are extracted in sterile water, 20 mM Tris-HCl, normal saline (0.15M NaCl), or other buffers as long as the conditions allow binding of the Invaplex 24 and Invaplex 50 fractions to the desired column.

It is preferable to delete detergents in the extraction solution since detergents tend to form mixed micelles (micelles containing a variety of proteins) which may not behave in a consistent manner on the ion-exchange column. Detergents will also solubilize integral membrane proteins which may interfere with the Invaplex product. Finally, detergents may disrupt or denature the Invaplex and solubilize all of the indivdual components of the complex. Sterile water can be prepared by methods known in the art, for example, filtering through a 0.10, 0.22 or 0.45 micron filters. The concentration of bacterial cells to water is preferably $1\times10^7$ to about $2\times10^{12}$ cells per ml of water or buffer, more preferably between $1\times10^8$ to about $2\times10^{11}$.

Extraction time is preferably regulated since if it is too long degradation of product may result, and too short will result in poor yield of product.

A protease inhibitor can be added, during the extraction step to aid in reducing the protein degradation of the final product. Examples of proteases which could be added include phenylmethylsulfonyl fluoride (PMSF). Other protease inhibitors are available such as serine protease inhibitors but they are usually somewhat toxic. If the invaplex is to be administered to living cells, it would be preferable to delete the protease inhibitors or remove it from solution prior to administration due to the toxicity of the protease inhibitors. However, if the Invaplex is to be used for an ELISA reagent, the protease inhibitor could be left in the solution, in fact it would be preferable to have it in the solution.

Next, the cells and membrane fragments are removed from the solution by methods known in the art such as centrifugation, filtration, microfiltration, ultrafiltration, however, ultracentrifugation is preferable for removing the small membrane fragments before the solution is subjected ion-exchange chromatography. Following extraction, the complex may be separated from the cellular debris by any technique suitable for separation of particles in complex mixtures. The complex may then be purified by anion or cation exchange chromatography or other isolation techniques which may include, but are not limited to, ammonium sulfate or ethanol precipitation, acid extraction, electrophoresis, isoelectric focusing, immunoadsorption, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography. Anion exchangers include diethylaminoethyl (DEAE) {—OCH2CH2N+H(CH2CH3)2}; quaternary aminoethyl (QAE){—OCH2CH2N+(C2H5)—CH2CHOH—CH3}; and quaternary ammonium (Q){—OCH2CHOH—CH3CHOH—CH2N+(CH3)C3}. Such functional groups are bound to various supports, each support varying in particle size, but also vary with respect to the support material. Examples of support material include:Monobeads,10 um bead of hydrophilic polystyrene/divinylbenzene {i.e., Mono Q (Pharmacia, Upsula, Sweden)}, Minibeads, 3 um bead of a hydrophilic polymer {i.e., Mini Q (Pharmacia)} SOURCE, 15 & 30 um monodispersed hydrophilized rigid, polystyrene/divinylbenzene beads {i.e., SOURCE Q (Pharmacia)} Sepharose, 34–50 um highly crosslinked agarose beads {i.e., HiTrap Q (Pharmacia) and Econo-Pac High Q (Bio-Rad)} Sepharose Fast Flow, 90 um agarose beads {i.e., QSepharose Fast Flow (Pharmacia)}, Sepharose Big Beads, 100–300 um agarose beads {i.e., QSepharose Big Beads (Pharmacia)}.

The chloride ion (Cl—) is the counterion of choice for anion exchange chromatography, with the choice of buffer dependent on the required pH interval. While Tris has a an effective buffering range of 7.6 to 8.0. Other buffers which may be used include: N-methyl-diethanolamine (pH 8.0–8.5), diethanolamine (pH 8.4–8.8), 1,3-diaminopropane (pH 8.5–9.0), ethanolamine (pH 9.0–9.5), and potentially piperazine (pH 9.5–9.8). These buffers are used at a low concentration, usually 20 mM, but could be as high as 50 mM.

Other columns or methods may be used as long as they maintain native structure of the Invaplex so that immunogenicity and function is intact, allow large volumes of a dilute protein solution to be loaded and concentrated, the buffers are biologically compatible, the method is rapid in order to minimize degradation of product and few processing steps are required.

It is preferable that each column be dedicated to a specific serotype and strain of Shigella. The optimal protein concentration in the final product would be approximately 10 doses per ml. But the range could be as low as 0.1 dose per ml (protein conc. of 2.5 ug/ml) up to much higher levels of 5000 doses per ml (protein conc. of 125 mg/ml) as long as solubility is maintained, i.e. concentration not too high to cause precipitation and not too low to make filtration too costly and time consuming.

Ideally we are achieving 0.25 mg/ml to 5 mg/ml in peak fractions of Invaplex 24 and Invaplex 50. If protein conc. is less than 0.25mg/ml than it must be concentrated by centrifugal size-exclusion filtration (mw cutoff of 10000 to 100,000 more preferably 30,000 mw cutoff).

Using the method described in the Materials and Methods below, the fractions containing the greatest amount of IpaB and IpaC were found in fractions eluted at 24% buffer and 50% buffer from the ion-exchange column, resulting in Invaplex 24, and Invaplex 50.

This method needs to be modified minimally for use with other gram-negative bacteria. For example, other ion-exchange columns can be used, and different antibodies must be used to probe for the target antigens. For example, antibodies for SipB and SipC would have to be used to identify peak fractions containing the complex obtained from Salmonella spp. Yersinia would need anti YOP protein antibodies (Corneliz and Wolf-Watz, 1997, *Mol. Microbiol.* 23, 861–867).

Other methods for producing Invaplex include methods whereby individual invasin proteins are combined with LPS in order to form a complex with a native configuration. In addition, the invasins/LPS complex can be further purified from other components in the Invaplex 24 and Invaplex 50 fractions by purification techniques as desribed above and below.

In one embodiment, the present invention relates to a vaccine for protection against gram-negative bacteria. The vaccine comprises Invaplex from a gram-negative bacteria. The vaccine can be prepared by isolating Invaplex using methods described in detail above or below. One or more isolated Invaplex is prepared for administration to mammals by methods known in the art, which can include filtering to sterilize the solution, diluting the solution, adding an adjuvant and stabilizing the solution. One particular advantage of the present invention is that Invaplex preparations do not need to be administered with an immunopotentiator such as an adjuvant or a carrier, since the Invaplex itself functions as such. This characteristic as such does not preclude the use of immunopotentiators in compositions of the present invention. As such, in one embodiment, a composition of the present invention can include one or more Invaplexes and one or more adjuvants or carriers.

Adjuvants are typically substances that generally enhance the immune response of an animal to a specific antigen. Suitable adjuvants include, but are not limited to, Freund's adjuvant, other bacterial cell wall components, aluminum-based salts, calcium-based salts, silica, polynucleotides, toxoids, serum proteins, viral coat proteins, other bacterial-derived preparations, gamma interferon, block copolymer adjuvants, such as Hunter's Titermax adjuvant (CytRx™, Inc. Norcross, Ga.), Ribi adjuvants (availabe from Ribi ImmunoChem Research, Inc. Hamilton, Mo.), and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, oils, esters, and glycols.

The vaccine can be lyophilized to produce a vaccine against gram-negative bacteria in a dried form for ease in transportation and storage. The dried compositions can be used for oral delivery. Invaplexes can also be mixed with a pharmaceutically acceptable excipient, such as an isotonic buffer that is tolerated by the organism to be administered the vaccine. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, and Tris buffer, while examples of preservatives include thimerosal, m- or 0-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

Further, the vaccine may be prepared in the form of a mixed vaccine which contains the Invaplexes described above and at least one other antigen as long as the added antigen does not interfere with the effectiveness of the vaccine and the side effects and adverse reactions are not increased additively or synergistically. The vaccine can be associated with chemical moieties which may improve the vaccine's solubility, absorption, biological half life, etc. The moieties may alternatively decrease the toxicity of the vaccine, eliminate or attenuate any undesirable side effect of the vaccine, etc. Moieties capable of mediating such effects are disclosed in *Remington's Pharmaceutical Sciences* (1980). Procedures for coupling such moeities to a molecule are well known in the art.

The vaccine may be stored in a sealed vial, ampule or the like. The present vaccine can generally be administered in the form of a spray for intranasal administration, or by nose drops, inhalants, swabs on tonsils, or a capsule, liquid, suspension or elixirs for oral administration. In the case where the vaccine is in a dried form, the vaccine is dissolved or suspended in sterilized distilled water before administration.

Generally, the vaccine may be administered to a subject orally, subcutaneously, intradermally, transdermally, or intramuscularly but preferably intranasally or orally, rectally and vaginally in a dose effective for the production of neutralizing antibody and resulting in protection from infection or disease. By subject is meant an animal, bird, fish and mammal including humans. The vaccine may be in the form of single dose preparations or in multi-dose flasks which can be used for mass vaccination programs. Reference is made to *Remington's Pharmaceutical Sciences*, Mack Publising Co., Easton, Pa., Osol (ed.) (1980); and *New Trends and Developments in Vaccines*, Voller et al. (eds.), University Park Press, Baltimore, Md. (1978), for methods of preparing and using vaccines. Acceptable protocols to administer compositions in an effective manner include individual dose size, number of doses, frequencey of dose administration, and mode of administration. Determination of such protocols can be accomplished by those skilled in the art. A preferred single dose of an Invaplex composition is from about 0.1 ug/kg body weight to about 100 ug/kg body weight. Boosters are preferably administered when the immune response of an organism is no longer being effectively modulated. Such compositions can be administered from about two weeks to several years after the original administration. A preferred administration schedule is one in which from about 0.5 ug to about 10 ug of a composition per kg body weight of the organism is adminsitered from about one to about four times over a time period of from about one month to about 6 months.

In another embodiment, the present invention relates to a method of reducing gram-negative infection symptoms in a patient by administering to said patient an effective amount of Invaplex antibodies, including those made in humans, either polyclonal or combinations of monoclonals to Invaplex, as described above. When providing a patient with Invaplex antibodies, the dosage administered will vary depending upon such factors as the patient's age, weight, height, sex, general medical condition, previous medical history, etc. In general, it is desirable to provide the recipient with a dosage of the above compounds which is in the range of from about 1 pg/kg to 500 mg/kg (body weight of patient), although a lower or higher dosage may be administered.

The present invention also provides a kit comprising a pharmaceutical (for prophylaxis i.e. a vaccine or for therapy i.e. a therapeutic) as described above in a container preferably a pre-filled syringe or glass vial/ampoule with printed instructions on or accompanying the container concerning the administration of the pharmaceutical to a patient to prevent or treat conditions caused by gram-negative bacterial infections.

Described below are examples of the present invention which are provided only for illustrative purposes, and not to limit the scope of the present invention. Other suitable modifications and adaptations of the variety of conditions and parameters normally encountered in this art which are obvious to those skilled in the art are within the spirit and scope of the present invention.

The following methods and materials were used in the examples below.

Bacterial Growth and Strains.

Most of the Shigella strains used in these studies are part of the WRAIR collection. They include *Shigella flexneri* 5 (M90T-W and Inc103, both are vir+), S. flexneri 5 (M90T-55, vir−), *S. flexneri* 2a (2457T), *S. sonnei* (Mosley), *S. dysenteriae* 1 (Ubon), and enteroinvasive *Escherichia coli* (0152). *S. boydii* 2 (CDC strain 3057–98) was kindly provided by N. Strockbine.

Isolated Shigella colonies were used to inoculate 50 mls of PenAssay (Antibiotic Medium #3, Difco) broth at 37° C. After 4 hrs of growth, 10 mls of the log phase culture were added to each liter of prewarmed (37° C.) PenAssay broth to be used for overnight growth. The 1 liter cultures were incubated overnight at 37° C. in a shaking incubator.

Water Extraction of Shigella Proteins.

A modification of the original water extraction procedure described by Oaks et al (Oaks et al, 1986, supra) was used to prepare the material from which the Shigella invasin complex was isolated. Identical procedures are used for enteroinvasive *E. coli*. Typically, four liters of an overnight culture of virulent shigellae were used for one batch of water extract. The bacterial cells were collected by centrifugation in a GS3 rotor (Sorvall), at 6000 rpm (apx 6000×g) for 30 min at 4° C. Next the bacterial cells were suspended in sterile, deionized water (0.45 um membrane filtered) at a volume of 50 mls per liter of overnight culture, and incubated at 37° C. in a shaking water bath (apx 200 rpm) for 2 hrs. After extraction with water, the cells were collected by centrifugation at 16000×g (GSA rotor, 10000 rpm) for 30 min at 4° C. The supernatant was collected and centrifuged at approximately 100,000×g for 1 hr at 4° C., to pellet membrane fragments. The 100,000×g supernatant was decanted into a sterile, pre-chilled flask, on ice. All 100,000×g supernatants for a single batch of water extract were pooled at this time. All samples were maintained on ice when possible and protease inhibitors were not used during the procedure. The water extract was stored at −70° C.

Characterization of Water Extract.

The total protein content of each batch of water extract was measured by the bicichoninic acid assay (Pierce Chemical Company, Rockford, Ill.). Water extract batches were also analyzed for the presence of IpaB, IpaC and IpaD by western blots or spot blots using IpaB (mab 2F1), IpaC (mab 2G2), and IpaD (mab 16F8) specific monoclonal antibodies (Mills et al, 1988; Turbyfill et al, 1998) to probe for the individual Ipa proteins. Only water extracts which were positive for the Ipa proteins were used for invasin complex purification.

FPLC (Fast Protein Liquid Chromatography).

Ion exchange chromatography was used to isolate invasin complex fractions from the water extract. A 5ml anion exchange HiTrapQ (Pharmacia, Uppsala, Sweden) column was equilibrated with 20 mM Tris-HCl, pH 9.0 (buffer A) at ambient temperature. Prior to loading, Tris-HCl (0.2 M, pH 9.0) was added to the water extract sample to a final concentration of 20 mM, after which 20 mls of the water extract was run through the column at a flow rate of 2 ml/min. After loading, the column was washed with 6 column volumes of buffer A. All elutions were carried out with step gradients consisting of 24% buffer B, followed by a 50% buffer B step, and finally the column was washed with 100% buffer B (1M NaCl in 20 mM Tris-HCl, pH 9.0). After washing with 100% buffer B, the column was reequilibrated with buffer A before the next run. Each column used in these studies was dedicated to a specific serotype and strain of Shigella. Protein passing through the column was monitored at 280 nm and 2 ml fractions were collected into polypropylene tubes. Data from the U.V. detector was recorded via the ADInstruments PowerChrom data acquisition and analysis software for the Macintosh computer operating system. Several FPLC runs were required for each water extract batch. As fractions were collected they were immediately placed at −70° C.

Each fraction was analyzed by immuno-spot blot for the presence of IpaC and IpaB. Fractions (usually 1 or 2) containing the greatest amount of IpaB & IpaC in the 24% buffer B were pooled as were peak Ipa protein fractions in the 50% buffer B step, resulting in Invaplex 24 and Invaplex 50 for a run. Invaplex 24 and Invaplex 50 run pools, once determined to be relatively similar with respect to IpaB, IpaC, & IpaD content (determined by western blot), LPS content (determined by silver stain analysis of gels, see below) and total protein composition, were combined for all runs from a particular batch of water extract. These final pools were aliquoted into 1.5 ml samples and stored at −80° C. and identified as a particular "lot" of Invaplex 24 or Invaplex 50.

ELISA using Water Extract, IpaC & IpaD, and LPS as Antigens.

ELISA assays were used to measure antibody levels to various antigens in animal sera (Oaks et al, 1986, supra; Turbyfill et al, 1998, supra). Antigens used include water extract from vir+ (M90T-W) and vir− (M90T-55) strains of S. flexneri 5; purified LPS S. flexneri 2a, S. flexneri 5, S. sonnei, S. dysentereiae 1, S. boydii 2, and enteroinvasive E. coli O152; and ovalbumin (Sigma Chemical Co.). Concentrations of antigen used in the assays were 1 ug/well (water extract, and LPS) and 0.5 ug/well for purified IpaC and IpaD. Antigens were diluted in carbonate coating buffer (0.2 M carbonate, pH 9.8) and added to polystyrene 96-well antigen plates (Dynex Technologies, Inc, Chantilly, Va.). Next the antigen was removed from the wells followed by the addition of 2% casein (2% casein in a Tris-saline buffer, pH 7.5) to block the plates. Primary antibodies were diluted in 2% casein and were incubated with the antigen for 2 hrs. After 4 washes in PBS (10.75 mM sodium phosphate, 145 mM NaCl) with 0.05% Tween 20, plates were probed with commercial anti-immunoglobulin IgG or IgA (diluted 1/500 in casein, Kirkgaard & Perry, Gaithersburg, MD) conjugated with alkaline phosphatase. The conjugates were diluted in the casein diluent. The substrate used in all ELISAs was para-nitrophenyl phosphate (1 mg/ml in 10% diethanolamine buffer, pH 9.8, containing 0.1 mg/ml $MgCl_2$ and 0.02% sodium azide). The optical density (O.D.) was measured at 405 nm on a Molecular Devices ELISA plate reader.

Electrophoresis and Western Blots.

Polyacrylamide gel electrophoresis was used for the separation and analysis of Shigella polypeptides and lipopolysaccaride. Gels for western blots and coomassie blue staining consisted of 13% acrylamide cross-linked with $N_1N^1$-diallytartardiamide, whereas gels for silver staining were cross-linked with bis-acrylamide. Western blots were performed as previously described (Oaks, et al, 1986, supra). Silver staining (Tsai and Reeves, 1982, Anal. Biochem. 119, 115–119) was used to stain LPS in samples treated with proteinase K prior to loading on gels (Hitchcock and Brown, 1983, J. Bacteriol. 154, 269–277). Antisera used in western blots included monoclonal antibodies to IpaB (2F1), IpaC (2G2) and IpaD (16F8) and monkey convalescent sera which contains antibodies to all Ipa proteins and VirG.

Immunogenicity of Invaplex 24 and Invaplex 50.

Small animals (guinea pigs or mice) were immunized with Invaplex 24 and Invaplex 50 to determine the immunogenicity and safety of these structures.

The ability of the Invaplex fractions to promote an immune response in Balb/c mice was tested in groups of 5 mice. Each mouse was immunized intranasally with 5 ug of Invaplex 24 or Invaplex 50 on days 0, 14, and 28. Diluent buffer was used to immunize control animals. A total antigen volume of 25 ul was delivered in 5 to 6 small drops applied to the external nares with a micropipet. Blood was taken by tail bleed from all mice on days 0, 21, and 35.

Guinea pigs (4 to 5 per group) were immunized intranasally with 25 ug/dose of either Invaplex 24 or Invaplex 50. Diluent buffer (0.9% saline) was used to immunize control animals. The antigen was applied to the external nares with a micropipet in a total volume of 50 ul per nostril. Guinea pigs were immunized on days 0, day 14, and day 28. Guinea pigs were bled on day 0, day 28, day 42, and 2 weeks after challenge, from the lateral ear vein. Prior to intranasal immunization guinea pigs and mice were anesthetized with ketamine/rompun.

Challenge of Guinea Pigs Immunized with with Invaplex 24 or Invaplex 50.

Three weeks after the 3rd immunization, guinea pigs were challenged intraocularly with S. flexneri 5 (M90T-W)($3.6 \times 10^8$cfu), S. flexneri 2a (2457T ($6.0 \times 10^8$cfu), S. sonnei (Mosley) ($4.1 \times 10^8$cfu), S. dysenteriae 1 ($4.8 \times 10^8$cfu), S. boydii 2 ($5.2 \times 10^8$cfu ), or enteroinvasive E. coli O152 ($5.8 \times 10^8$cfu ). Animal were observed daily for 5 days for the occurrence of keratoconjunctivitis. Scoring of the degree of inflammation and keratoconjunctivitis has been previously described (Hartman, et al., 1991, Infect. Immun. 59, 4075–4083).

EXAMPLE 1

Isolation and Characterization of Invaplex 24 and Invaplex 50.

In initial experiments, the water extracted material was eluted from an FPLC ion-exchange column with continuous 0 to 1.0 M NaCl gradients in 20 mM Tris, pH 9.0. It was found that the majority of the IpaB and IpaC proteins consistently eluted in two peaks at approximately 24% buffer B and 50% buffer B (data not shown). Therefore, step gradients of 24% buffer B, 50% buffer B, and a final wash at 100% buffer B were used in all subsequent elutions.

Figure 2:
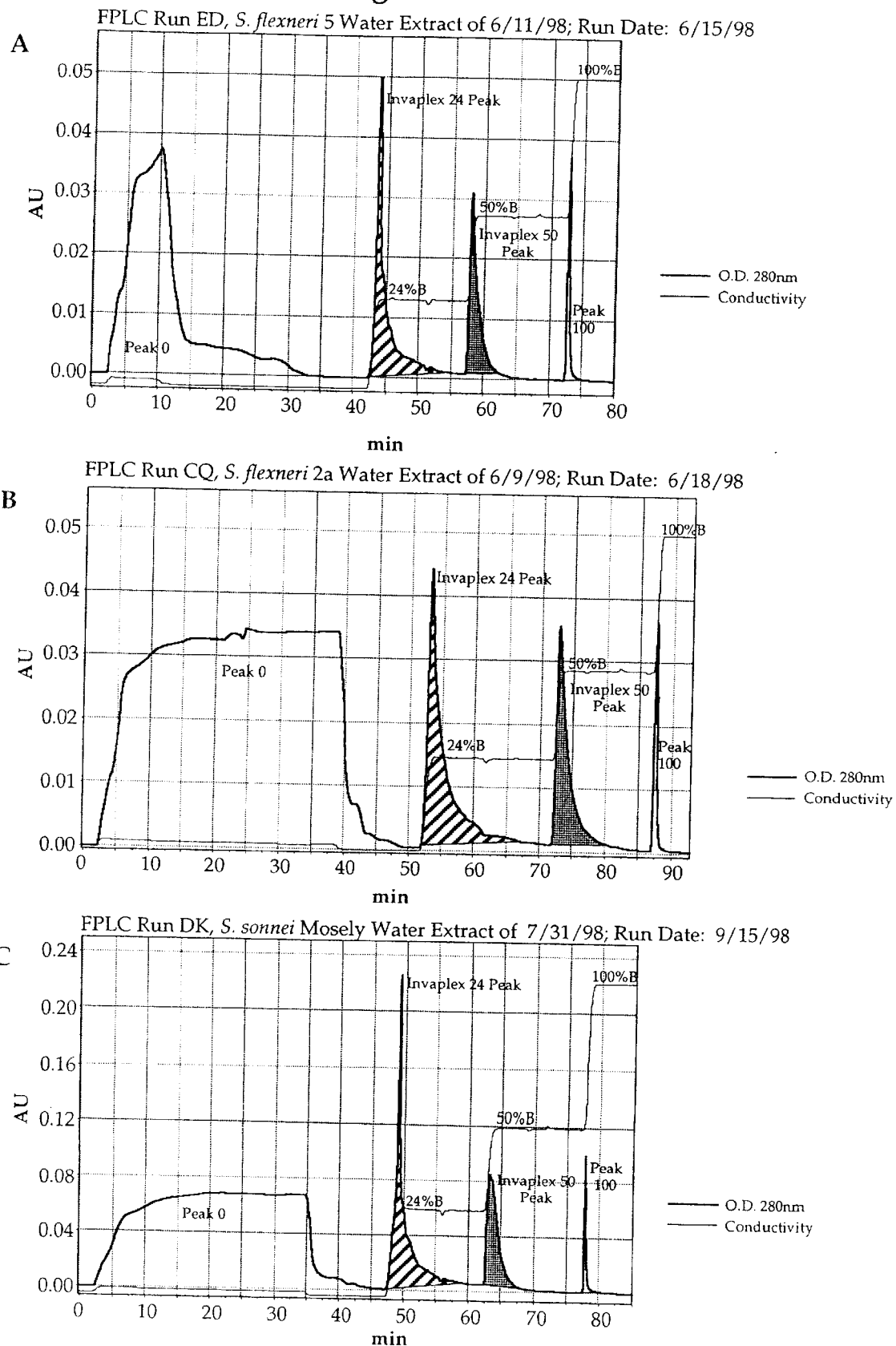
FIGS. 2A–2C. FPLC chromatographs of Invaplex purification by ion-exchange chromatography from *Shigella flexneri* 5, *S. flexneri* 2a, *S. sonnei*, *S. dysenteriae* 1, *S. boydii* 2, and enteroinvasive *Escherichia coli* O152. FPLC ion-exchange chromatography of water-extracted proteins prepared from *Shigella flexneri* 5 (panel A), *S. flexneri* 2a (panel B), *S. sonnei* (panel C), *S. dysenteriae* 1 (panel D), *S. boydii* 2 (panel E), and enteroinvasive *Escherichia coli* O152 (panel F) were separated on 5 ml columns of anion exchange resin HiTrapQ (Pharmacia). Two tracings are plotted; one is the optical density (O.D.) at 280 (AU, thick line) which shows the four protein peaks; the other tracing is plotting the conductivity or % buffer B (1 M NaCl in 20 mM Tris-HCl, pH 9.0) and clearly shows the 24%, 50%, and 100% buffer B steps. The flow rate was 2.0 ml/min and 2 ml fractions were collected throughout the run. The Invaplex 24 and Invaplex 50 peaks are labeled. These fractions are collected and used in further experiments. All fractions are analyzed for IpaC and IpaB content by spot blot. Peak IpaC and IpaB content is in the Invaplex 24 and Invaplex 50 peak fractions.

Typical chromatographs for water extracts from *S. flexneri* 5, *S. flexneri* 2a, *S. sonnei*, *S. dysenteriae* 1, *S. boydii* 2, and enteroinvasive *E. coli* O152 separated by FPLC into the invasin complex peaks are in FIG. 2. The Invaplex 24 peak and Invaplex 50 peak are labeled for each chromatograph. Peak 0 (zero % buffer B) represents protein that did not bind to the HiTrapQ anion-exchange column. A 100% buffer B peak (peak 100) is also indicated. Each fraction was evaluated by immuno spot blot with IpaB and IpaC Mabs. The fractions containing most of the IpaB and IpaC activity were in the Invaplex 24 and Invaplex 50 peaks. This FPLC profile is reproducible in that identical results are obtained with the same batches of water extract, with different batches of water extract, and with water extracts from all four species of Shigella as well as enteroinvasive *E. coli* (see FIG. 2). Typical yields of Invaplex 24 and Invaplex 50 are approximately 5 mg and 1 mg, respectively, per liter of original culture.

The consistency of different FPLC runs of purified Invaplex 24 or Invaplex 50 was evalauated by western blots and by silver stained polyacrylamide gels. The silver stained gels confirm the overall consistency of each FPLC run. It was also possible to show that the same antigenic composition (for example the presence of IpaB, IpaC, IpaD) was present in Invaplex 24 or Invaplex 50 preparations purified at different times (data not shown). Each Invaplex 24 preparation is identical as are each of the Invaplex 50 preparations.

Figure 3:
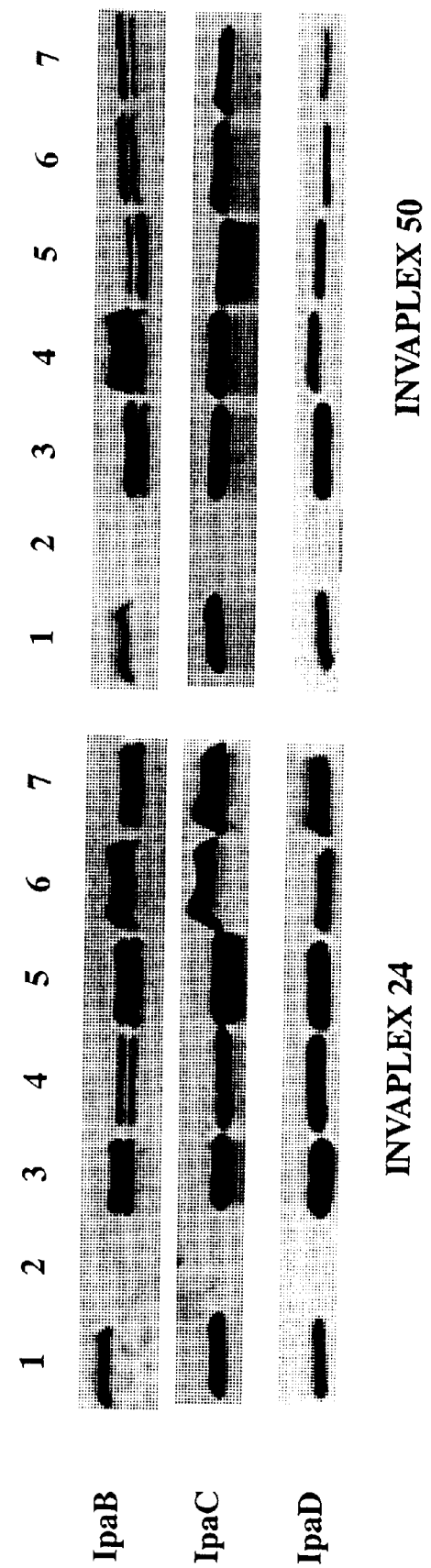
FIG. 3. Western blot analysis of Invaplex 24 and Invaplex 50 from *S. flexneri* 2a, *S. sonnei*, *S. dysenteriae* 1, *S. boydii* 2, and enteroinvasive *E. coli* O152 with monoclonal antibodies against IpaB, IpaC and IpaD. Samples run on this gel are, whole-cell lysates of *S. flexneri* 5, M90T-Wash, vir+ (lane 1), whole-cell lysates of *S. flexneri* 5, M90T-55, vir− (lane 2), and Invaplex 24 (left panel) or Invaplex 50 (right panel) from *S. flexneri* 2a (lane 3), *S. sonnei* (lane 4), *S. dysenteriae* 1 (lane 5), *S. boydii* 2 (lane 6), and enteroinvasive *E. coli* O152 (lane 7). This is a composite of western blots probed with monoclonal antibodies reactive with IpaB (Mab 2F1), IpaC, (Mab 2G2) and IpaD (Mab 16f8). The IpaB, IpaC and IpaD bands are noted. Each lane containing Invaplex preparations was loaded with 20 ug protein.

Invaplex preparations from different Shigella serotypes were also evaluated and compared to determine if the Invaplex composition varied from one species to another. FIG. 3 is a composite of several western blots of Invaplex 24 and Invaplex 50 preparations probed for different antigens with monoclonal antibodies against IpaB, IpaC and IpaD (FIG. 3). The Invaplex 24 and Invaplex 50 preparations from *S. flexneri* 5, *S. flexneri* 2a, *S. sonnei*, *S. dysenteriae*, *S. boydii* and enteroinvasive *E. coli* all contained IpaB, IpaC, and IpaD. Both Invaplex 24 and Invaplex 50 also contained IpaA. One difference between the Invaplex 24 and Invaplex 50 preparations is that the Invaplex 24 samples contain relatively more IpaD than do the Invaplex 50 preparations (Table 1). In addition, the Invaplex 50 preparations contain VirG* (a truncated form of the 120 kDal VirG protein). VirG* has not been detected in Invaplex 24 fractions by the methods used. Additional proteins are present in the Invaplex preparations but their identities are not known.

Lipopolysaccharide can be detected by silver staining polyacrylamide gels. If samples are treated first with proteinase K to digest all proteins, then only the LPS will be present in the samples. Silver stained gels of Invaplex 24 and Invaplex 50 preparations from all Shigella spp and enteroinvasive *E. coli* before and after proteinase K treatment show a typical LPS core (a prominant band at the bottom of the gel) for both Invaplex 24 and Invaplex 50 samples. In addition, other LPS bands at gradually increasing molecular sizes (representing varying degrees of biosynthesis of the O-side chains onto the core) were also present. Similar LPS profiles were present in Invaplex 24 and Invaplex 50 preparations from *S. flexneri*, *S. boydii*, *S. dysenteriae* and enteroinvasive *E. coli*. The LPS content of Invaplex 24 from *S. sonnei* was lower than that of other Invaplex preparations. Invaplex 50 from *S. sonnei* was similar to that of other Invaplex 50 preparations.

A summary of the various antigenic proteins and LPS in the Invaplex 24 and Invaplex 50 preparations for each species are in Table 1.

TABLE 1A

Summary of Antigen Content in Invaplex 24
Preparations Based on Western Blot Analysis or Silver Stained Polyacrylamide Gels

| | IpaD[1] | IpaB[1] | IpaC[1] | LPS[2] | IpaA[1] | VirG*[1] |
|---|---|---|---|---|---|---|
| *S. flexneri* 2a | ++[3] | ++ | ++ | + | + | – |
| *S. sonnei* | ++ | + | ++ | +/– | + | – |
| *S. boydii* 2 | + | ++ | ++ | + | + | – |
| *S. dysenteriae* 1 | ++ | ++ | ++ | + | + | – |
| EIEC[4] | +/– | ++ | ++ | + | + | + |

TABLE 1B

Summary of Antigen Content in Invaplex 50
Preparations Based on Western Blot Analysis or Silver Stained Polyacrylamide Gels

| | IpaD[1] | IpaB[1] | IpaC[1] | LPS[2] | IpaA[1] | VirG*[1] |
|---|---|---|---|---|---|---|
| *S. flexneri* 2a | ++[3] | + | ++ | + | + | ++ |
| *S. sonnei* | + | ++ | ++ | + | + | ++ |
| *S. boydii* 2 | + | + | ++ | + | + | ++ |
| *S. dysenteriae* 1 | + | + | ++ | + | + | ++ |
| EIEC[4] | + | + | ++ | + | + | ++ |

[1]These results are based on western blots using monoclonal sera against IpaD, IpaB, and IpaC, or monkey convalescent sera which contains antibodies against all Ipa proteins and also VirG (and VirG*, a truncated form of VirG)
[2]LPS was detected in proteinase K treated samples run on polyacrylamide gels stained with silver
[3]Scoring is graded as follows: "++" indicates a strongly positive reaction on the western blot; "+" is a positive reaction; "+/–" is a weak reaction; and "–" is a negative reaction.
[4]EIEC = enteroinvasive *E. coli*.

EXAMPLE 2

Immunogenicity and Safety of Invaplex 24 and Invaplex 50

Guinea pigs were immunized with Invaplex 24 or Invaplex 50 to determine the immunogenicity and safety of these structures and the individual components within the Invaplex preparations.

Guinea pigs immunized with Invaplex 24 or Invaplex 50 prepared from each of the four Shigella species or EIEC responded with increased serum antibodies to several different Shigella antigens (see Table 2 and 3). The guinea pigs were immunized with 3, 25 ug doses administered intranasally every two weeks.

Invaplex 24 immunized guinea pigs produced a strong IgG response to LPS after three intranasal immunizations (table 2A). IgA to LPS was also produced after immunization with Invaplex 24 (Table 2B). Unlike the other Invaplex 24 preparations, animals immunized with *S. sonnei* Invaplex 24 produced a minimal titer against LPS. This supports data indicating that the Invaplex 24 from *S. sonnei* has less LPS than Invaplex 24 preparations from other Shigella spp. Even so, upon challenge with virulent *S. sonnei*, the *S. sonnei* Invaplex 24 animals produced a strong IgG and IgA response to LPS indicating that the immune system had been primed for an anti-LPS immune response by vaccination with Invaplex 24.

Invaplex 24 preparations stimulated a strong reaction with the vir+ water extract antigen and only a minimal response to the vir– water extract antigen (Table 2C and 2D). This is very similar to the virulent-specific immune response generated after infection with shigellae in humans or monkeys. Invaplex 24 preparations from all Shigella species tested stimulated a serum IgG response in guinea pigs. Upon challenge, the animals all showed a tremendous boost in antibody levels to the water extract indicating a successful priming by the Invaplex 24 vaccine. The boost in antibody levels was much higher than control animals treated with buffer and then challenged with shigellae.

Sera from guinea pigs immunized with Invaplex 24 were also measured for antibodies against the homologous Invaplex 24 and Invaplex 50 antigens used for vaccination. Thus if a group of animals were immunized with *S. flexneri* Invaplex 24, ELISAs were performed using *S. flexneri* Invaplex 24 and *S. flexneri* Invaplex 50 (see tables 2E and 2F). As expected the guinea pigs responded by producing antibodies to the immunizing Invaplex antigen. In most groups the antibody levels were greater for the identical Invaplex 24 antigen than for the Invaplex 50 antigen prepared from the same Shigella serotype. This provides furthur evidence that the Invaplex 24 and Invaplex 50 preparations are not identical. As seen before the *S. sonnei* Invaplex 24 immunized animals did not produce high levels of antibody after 3 immunizations but upon challenge with virulent *S. sonnei* they were able to mount an impressive memory response, again indicating that the Invaplex vaccine provides ample stimulus for the immune system.

Guinea pigs immunized with Invaplex 50 had strong antibody responses against water extract antigens (both vir+ and vir–) and LPS (Tables 3A-3F). The LPS responses elicited by Invaplex 50 vaccines (Table 3A and 3B) appeared comparable to that generated by the Invaplex 24 vaccine. Each group (except the *S. dysenteriae* Invaplex 50) produced anti-LPS IgG and IgA antibodies after 3 doses. Interestingly, animals immunized with the *S. sonnei* Invaplex 50 or the EIEC Invaplex 50 produced detectable IgG and IgA against LPS after just two immunization doses. Guinea pigs immunized with the *S. dysenteriae* Invaplex 50 produced minimal antibody levels against LPS however, upon challenge these animals did produce a dramatic increase in anti-LPS IgG, indicating that the Invaplex 50 vaccine was sucessful in priming these animal's immune system.

Invaplex 50 for all preparations from the different Shigella species and EIEC elicited a strong serum IgG response reactive with the water extract antigen (Tables 3C and 3D). Measureable IgG antibodies were present in each Invaplex 50 group after two doses of vaccine. This is somewhat better than that seen with the Invaplex 24 vaccines. Another difference is that the Invaplex 50 vaccines stimulated antibodies that were reactive with the water extract from a vir– shigellae. This is very likely due to antibodies being produced to non-plasmid encoded proteins which are present in the Invaplex 50 vaccine and not present or in low concentrations in the Invaplex 24 vaccine. Even so when the sera from Invplex 50 immunized animals are analyzed by western blots, it clear that antibodies to IpaC and IpaB are present. Thus, even though the immune response elicited by the Invaplex 50 vaccine doesn't appear to be virulent specific by the water extract ELISA (like that seen with Invaplex 24 or a natural infection) it does stimulate the production of antibodies to virulence proteins.

Sera from the Invaplex 50 immunized animals were also tested in ELISAs using Invaplex 50 or Invaplex 24 as the ELISA antigen (Table 3E and 3F). As seen with the Invaplex 24 vaccine, Invaplex 50 immunized animals produced high levels of IgG antibodies reactive with the immunizing Invaplex 50 antigen. Antibodies were detected after just two doses for all serotypes. Also a positive response was found against the Invaplex 24 antigen but for the most part the antibody levels were lower than that measured by the Invaplex 50 antigen. Again, this is evidence that the Invaplex 50 and Invaplex 24 contain different antigens and stimulate antibodies with somewhat different specificities.

TABLE 2

Serum Immune Response to Select Antigens in Guinea Pigs Immunized with Invaplex 24

| DAY | *S. flexneri* 2a | *S. flexneri* 5 | *S. sonnei* | *S. dysenteriae* | *S. boydii* | EIEC |
|---|---|---|---|---|---|---|
| A. Serum IgG antibody response to homologous LPS in guinea pigs immunized with Invaplex 24 from different Shigella species or EIEC | | | | | | |
| 0 | .021 ± .001 | .023 ± .002 | .023 ± .001 | .023 ± .001 | .033 ± .006 | .057 ± .005 |
| 28 | .083 ± .033 | .093 ± .065 | .026 ± .001 | .025 ± .002 | .043 ± .009 | .074 ± .012 |
| 42 | 1.129 ± .366 | .607 ± .352 | .034 ± .007 | .333 ± .246 | .042 ± .004 | .216 ± .092 |
| 56 | 2.976 ± .079 | 2.567 ± .4 | .621 ± .363 | 2.039 ± .508 | .111 ± .048 | .352 ± .135 |
| Control 0 | .021 ± .002 | .024 ± .002 | .024 ± .001 | .022 ± .0004 | .050 ± .006 | .039 ± .005 |
| Control 56 | .023 ± .001 | .477 ± .163 | .042 ± .009 | .023 ± .001 | .053 ± .009 | .066 ± .009 |
| B. Serum IgA antibody response to homologous LPS in guinea pigs immunized with Invaplex 24 from different Shigella species or EIEC | | | | | | |
| 0 | Not Done | Not Done | .038 ± .001 | .025 ± .001 | .024 ± .001 | .069 ± .004 |
| 28 | Not Done | Not Done | .041 ± .002 | .029 ± .003 | .034 ± .009 | .109 ± .023 |
| 42 | Not Done | Not Done | .072 ± .017 | .111 ± .061 | .042 ± .007 | .162 ± .041 |
| 56 | Not Done | Not Done | 1.086 ± .192 | .383 ± .114 | .349 ± .103 | .310 ± .097 |
| Control 0 | Not Done | Not Done | .034 ± .001 | .025 ± .001 | .023 ± .001 | .088 ± .005 |
| Control 56 | Not Done | Not Done | .165 ± .056 | .035 ± .004 | .035 ± .003 | .132 ± .007 |
| C. Serum IgG antibody response to Water Extract Antigen (Vir+) in guinea pigs immunized with Invaplex 24 from different Shigella species or EIEC | | | | | | |
| 0 | .041 ± .010 | .048 ± .007 | .077 ± .017 | .045 ± .007 | .063 ± .012 | .069 ± .005 |
| 28 | .850 ± .303 | .047 ± .008 | .072 ± .004 | .061 ± .024 | .098 ± .017 | .191 ± .111 |
| 42 | 1.984 ± .182 | .194 ± .074 | .116 ± .022 | .713 ± .142 | .471 ± .180 | 1.240 ± .439 |

TABLE 2-continued

Serum Immune Response to Select Antigens in Guinea Pigs Immunized with Invaplex 24

| DAY | S. flexneri 2a | S. flexneri 5 | S. sonnei | S. dysenteriae | S. boydii | EIEC |
|---|---|---|---|---|---|---|
| 56 | 2.985 ± .035 | 1.807 ± .283 | .366 ± .190 | 1.742 ± .613 | .688 ± .268 | 1.426 ± .588 |
| Control 0 | .036 ± .006 | .052 ± .017 | .091 ± .019 | .056 ± .006 | .078 ± .004 | .077 ± .009 |
| Control 56 | .377 ± .131 | .93 ± .204 | .072 ± .017 | .135 ± .075 | .048 ± .017 | .059 ± .016 |
| D. Serum IgG antibody response to Water Extract Antigen (Vir−) in Gguinea pigs immunized with Invaplex 24 from different Shigella species or EIEC ||||||||
| 0 | .069 ± .027 | .044 ± .009 | .074 ± .015 | .046 ± .003 | .061 ± .011 | .074 ± .012 |
| 28 | .073 ± .007 | .047 ± .01 | .066 ± .022 | .045 ± .005 | .075 ± .007 | .083 ± .007 |
| 42 | .072 ± .016 | .22 ± .155 | .117 ± .014 | .073 ± .011 | .097 ± .013 | .189 ± .029 |
| 56 | .331 ± .116 | 1.851 ± .387 | .679 ± .256 | .280 ± .034 | .129 ± .041 | .169 ± .037 |
| Control 0 | .037 ± .003 | .036 ± .006 | .062 ± .009 | .043 ± .004 | .059 ± .002 | .086 ± .013 |
| Control 56 | .247 ± .080 | .406 ± .051 | .078 ± .021 | .169 ± .117 | .041 ± .012 | .060 ± .016 |
| E. Serum IgG antibody response to Invaplex 24 in guinea pigs immunized with Invaplex 24 from different Shigella species or EIEC ||||||||
| 0 | .042 ± .004 | Not Done | .034 ± .003 | .049 ± .003 | .025 ± .001 | .021 ± .001 |
| 28 | .259 ± .108 | Not Done | .040 ± .002 | .072 ± .020 | .042 ± .007 | .020 ± .001 |
| 42 | .808 ± .281 | Not Done | .047 ± .008 | .506 ± .074 | .260 ± .103 | .020 ± .001 |
| 56 | 3.269 ± .038 | Not Done | .140 ± .037 | 1.539 ± .406 | 1.097 ± .369 | .959 ± .371 |
| Control 0 | .067 ± .014 | Not Done | .037 ± .003 | .039 ± .003 | .055 ± .010 | .036 ± .002 |
| Control 56 | .216 ± .071 | Not Done | .046 ± .004 | .066 ± .017 | .084 ± .020 | .061 ± .005 |
| F. Serum IgG antibody response to Invaplex 50 in guinea pigs immunized with Invaplex 24 from different Shigella species or EIEC ||||||||
| 0 | .044 ± .006 | Not Done | .043 ± .004 | .047 ± .012 | .037 ± .005 | .022 ± .001 |
| 28 | .132 ± .052 | Not Done | .035 ± .002 | .069 ± .024 | .044 ± .002 | .022 ± .001 |
| 42 | .404 ± .146 | Not Done | .057 ± .009 | .223 ± .057 | .101 ± .022 | .023 ± .001 |
| 56 | 2.462 ± .261 | Not Done | .424 ± .122 | .909 ± .299 | .806 ± .213 | .678 ± .278 |
| Control 0 | .049 ± .003 | Not Done | .042 ± .003 | .053 ± .004 | .040 ± .004 | .034 ± .004 |
| Control 56 | .0751 ± .107 | Not Done | .100 ± .010 | .155 ± .020 | .066 ± .012 | .073 ± .018 |

Different groups of 5 guinea pigs were immunized intranasally on day 0, 14, and 28 with Invaplex 24 prepared from either S. flexneri 2a S. flexneri 5, S. sonnei, S dysenteriae, S. boydii 2, or enteroinvasive E. coli (EIEC). The Invaplex source is listed at the top of each column. Antigens used in the ELISAs included LPS (table 2A and 2B) prepared from the homologous Shigella serotype from which the Invaplex vaccine was prepared; water extract (table 2C and 2D) was from S. flexneri 5 vir+ and vir−; and Invaplex 24 (table 2E) and Invaplex 50 (table 2F) were prepared from the same serotype from which the immunizing Invaplex was prepared. The serum IgG levels were measured for each of these antigens by ELISA. The serum IgA levels were solely determined for LPS. Blood was taken from all guinea pigs at 4 different time points, pre-treatment (day 0), post-2nd immunization (day 28), after 3 immunizations (day 42) and 1 week post-challenge (day 56). Animals were challenged with the same Shigella serotype from which the Invaplex vaccine was derived. The values for each timepoint represents the mean O.D.$_{405}$ ± S.E.M. for each group of 5 guinea pigs.

TABLE 3

Serum Immune Response to Select Antigens in Guinea Pigs Immunized with Invaplex 50

| DAY | S. flexneri 2a | S. flexneri 5 | S. sonnei | S. dysenteriae | S. boydii | EIEC |
|---|---|---|---|---|---|---|
| A. Serum IgG antibody response to homologous LPS in guinea pigs immunized with Invaplex 50 from different Shigella species or EIEC ||||||||
| 0 | .023 ± .001 | .035 ± .01 | .024 ± .0002 | .023 ± .0004 | .047 ± .004 | .066 ± .009 |
| 28 | .025 ± .004 | 0.054 ± .009 | .263 ± .083 | .023 ± .001 | .057 ± .014 | .168 ± .056 |
| 42 | .278 ± .104 | .913 ± .229 | 1.347 ± .296 | .039 ± .013 | .374 ± .200 | .736 ± .207 |
| 56 | .813 ± .189 | 2.931 ± .283 | 2.451 ± .286 | .592 ± .301 | .559 ± .272 | .916 ± .291 |
| Control 0 | .021 ± .002 | .024 ± .002 | .024 ± .001 | .022 ± .0004 | .050 ± .006 | .039 ± .005 |
| Control 56 | .023 ± .001 | .477 ± .163 | .042 ± .009 | .023 ± .001 | .053 ± .009 | .066 ± .009 |
| B. Serum IgA antibody response to homologous LPS in guinea pigs immunized with Invaplex 50 from different Shigella species or EIEC ||||||||
| 0 | Not Done | Not Done | .037 ± .001 | .024 ± .001 | .023 ± .001 | .120 ± .02 |
| 28 | Not Done | Not Done | .142 ± .026 | .025 ± .002 | .071 ± .024 | .287 ± .079 |

TABLE 3-continued

Serum Immune Response to Select Antigens in Guinea Pigs Immunized with Invaplex 50

| DAY | S. flexneri 2a | S. flexneri 5 | S. sonnei | S. dysenteriae | S. boydii | EIEC |
|---|---|---|---|---|---|---|
| 42 | Not Done | Not Done | .183 ± .025 | .161 ± .129 | .179 ± .059 | .437 ± .101 |
| 56 | Not Done | Not Done | .567 ± .095 | .296 ± .139 | .535 ± .046 | .403 ± .055 |
| Control 0 | Not Done | Not Done | .034 ± .001 | .025 ± .001 | .023 ± .001 | .088 ± .005 |
| Control 56 | Not Done | Not Done | .165 ± .056 | .035 ± .004 | .035 ± .003 | .132 ± .007 |
| C. Serum IgG antibody response to Water Extract Antigen (Vir+) in guinea pigs immunized with Invaplex 50 from different Shigella species or EIEC | | | | | | |
| 0 | .040 ± .005 | .032 ± .003 | .100 ± .018 | .054 ± .003 | .130 ± .058 | .072 ± .005 |
| 28 | .198 ± .085 | .147 ± .038 | .996 ± .047 | .146 ± .047 | .281 ± .055 | .626 ± .141 |
| 42 | .629 ± .105 | 1.047 ± .153 | 2.347 ± .394 | .856 ± .327 | 1.078 ± .114 | 2.091 ± .219 |
| 56 | 1.914 ± .374 | 3.1 ± .091 | 2.956 ± .280 | 1.836 ± .305 | .817 ± .217 | 2.689 ± .284 |
| Control 0 | .036 ± .006 | .052 ± .017 | .091 ± .019 | .056 ± .006 | .078 ± .004 | .077 ± .009 |
| Control 56 | .377 ± .131 | .93 ± .204 | .072 ± .017 | .135 ± .075 | .048 ± .017 | .059 ± .016 |
| D. Serum IgG antibody response to Water Extract Antigen (Vir−) in guinea pigs immunized with Invaplex 50 from different Shigella species or EIEC | | | | | | |
| 0 | .041 ± .005 | .03 ± .003 | .083 ± .013 | .040 ± .002 | .102 ± .039 | .071 ± .006 |
| 28 | .113 ± .040 | .145 ± .044 | 1.014 ± .431 | .131 ± .040 | .225 ± .029 | .511 ± .147 |
| 42 | .497 ± .237 | 1.077 ± .189 | 1.888 ± .505 | .614 ± .225 | .829 ± .137 | 1.767 ± .191 |
| 56 | 1.000 ± .388 | 3.199 ± .097 | 2.465 ± .436 | 1.157 ± .258 | .576 ± .169 | 2.374 ± .319 |
| Control 0 | .037 ± .003 | .036 ± .006 | .062 ± .009 | .043 ± .004 | .059 ± .002 | .086 ± .013 |
| Control 56 | .247 ± .080 | .406 ± .051 | .078 ± .021 | .169 ± .117 | .041 ± .012 | .060 ± .016 |
| E. Serum IgG antibody response to Invaplex 24 in guinea pigs immunized with Invaplex 50 from different Shigella species or EIEC | | | | | | |
| 0 | .046 ± .005 | Not Done | .050 ± .006 | .131 ± .041 | .039 ± .003 | .029 ± .005 |
| 28 | .101 ± .045 | Not Done | .065 ± .009 | .132 ± .035 | .080 ± .031 | .070 ± .018 |
| 42 | .143 ± .030 | Not Done | .149 ± .020 | .140 ± .031 | .604 ± .253 | .225 ± .067 |
| 56 | 1.962 ± .224 | Not Done | .459 ± .030 | .695 ± .173 | 1.287 ± .176 | .739 ± .288 |
| Control 0 | .067 ± .014 | Not Done | .037 ± .003 | .039 ± .003 | .055 ± .010 | .036 ± .002 |
| Control 56 | .216 ± .071 | Not Done | .046 ± .004 | .066 ± .017 | .084 ± .020 | .061 ± .005 |
| F. Serum IgG antibody response to Invaplex 24 in guinea pigs immunized with Invaplex 50 from different Shigella species or EIEC | | | | | | |
| 0 | .050 ± .006 | Not Done | .067 ± .022 | .069 ± .008 | .049 ± .005 | .029 ± .003 |
| 28 | .149 ± .043 | Not Done | .333 ± .064 | .123 ± .024 | .106 ± .019 | .164 ± .031 |
| 42 | .389 ± .155 | Not Done | .742 ± .081 | .373 ± .116 | .925 ± .231 | .530 ± .060 |
| 56 | 2.201 ± .375 | Not Done | 1.573 ± .189 | .904 ± .221 | 2.187 ± .335 | 1.425 ± .313 |
| Control 0 | .049 ± .003 | Not Done | .042 ± .003 | .053 ± .004 | .040 ± .004 | .034 ± .004 |
| Control 56 | .751 ± .107 | Not Done | .100 ± .010 | .155 ± .020 | .066 ± .012 | .073 ± .018 |

Different groups of 5 guinea pigs were immunized intranasally on days 0, 14, and 28 with Invaplex 50 prepared from either *S. flexneri* 2a, *S. flexneri* 5, *S. sonnei*, *S. dysenteriae*, *S. boydii* 2, or enteroinvasive *E. coli* (EIEC). The Invaplex source is listed at the top of each column. Antigens used in the ELISAs included LPS (table 3A and 3B) prepared from the homologous Shigella serotype from which the Invaplex vaccine was prepared; water extract (table 3C and 3D) was from *S. flexneri* 5 vir+ and vir−; and Invaplex 24 (table 3E) and Invaplex 50 (table 3F) were prepared from the same serotype from which the immunizing Invaplex was prepared. The serum IgG levels were measured for each of these antigens by ELISA. The serum IgA levels were solely determined for LPS. Blood was taken from all guinea pigs at 4 different time points, pre-treatment (day 0), post-2nd immunization (day 28), after 3 immunizations (day 42) and 1 week post-challenge (day 56). Animals were challenged with the same Shigella serotype from which the Invaplex vaccine was derived. The values for each timepoint represents the mean O.D.$_{405}$ ± S.E.M. for each group of 5 guinea pigs.

In all of the guinea pig experiments control animals immunized with buffer diluent did not produce antibodies to any of the Shigella antigens tested. Upon challenge these animals produced much lower levels of antibodies than did those animals immunized with Invaplex 24 or Invaplex 50 vaccines.

EXAMPLE 3

Vaccination with Invaplex 24 and Invaplex 50 and Challenge of Animals with Virulent Shigellae.

A marked serum IgA and IgG response was produced in guinea pigs immunized with the Invaplex 24 and Invaplex 50 preparations. A minimal titer was produced after 2 immunizations, but a more pronounced titer is achieved with 3 immunizations, especially with Invaplex 50 (Tables 2 and 3). Antibodies were detected with ELISAs using either vir+ or vir− water extract antigens or purified LPS. Also of interest was the substantial boost in antibody levels that immunized animals exhibited upon challenge with virulent shigellae. This boost in titer indicates that the Invaplex vaccines successfully primed the mucosal immune system. Control animals, treated with buffer and then challenged, showed a much lower antibody response after infection with shigellae which resulted in full-blown keratoconjunctivitis.

Using the guinea pigs keratoconjunctivitis model, it was possible to prevent disease in guinea pigs immunized intranasally with either Invaplex 24 or Invaplex 50 (see Table 4 below). Homologous protection was seen with the Invaplex preparations produced from *S. flexneri* 2a, *S. flexneri* 5, *S. sonnei*, *S. boydii*, and enteroinvasive *E. coli*. In the case of *S. dysenteriae* good protection with Invaplex 24 was observed whereas the *S. dysenteriae* Invaplex 50 had a low level of protection.

The level of protection against disease in Invaplex immunized guinea pigs is comparable to that generated by existing experimental Shigella vaccines undergoing Phase I and Phase II trials. Immunization with either Invaplex preparation caused no visible distress to the animals.

TABLE 4

Protection in the Guinea Pig Keratoconjunctivits Model Using Invaplex 24 or Invaplex 50 Vaccines Prepared from Virulent Shigella or Enteroinvasive E. coli.

| VACCINE TREATMENT[1] | CHALLENGE AGENT[2] | # POSITIVE/ TOTAL[3] |
|---|---|---|
| S. flexneri 2a Invaplex 24 | S. flexneri 2a | 2/18 |
| S. flexneri 2a Invaplex 50 | S. flexneri 2a | 3/16 |
| Buffer Control | S. flexneri 2a | 15/15 |
| S. flexneri 5 Invaplex 24 | S. flexneri 5 | 1/8 |
| S. flexneri 5 Invaplex 50 | S. flexneri 5 | 0/10 |
| Buffer Control | S. flexneri 5 | 9/10 |
| S. sonnei Invaplex 24 | S. sonnei | 2/10 |
| S. sonnei Invaplex 50 | S. sonnei | 0/10 |
| Buffer Control | S. sonnei | 9/10 |
| S. dysenteriae I Invaplex 24 | S. dysenteriae I | 4/10 |
| S. dysenteriae I Invaplex 50 | S. dysenteriae I | 7/10 |
| Buffer Control | S. dysenteriae I | 9/10 |
| S. boydii 2 Invaplex 24 | S. boydii 2 | 2/10 |
| S. boydii 2 Invaplex 50 | S. boydii 2 | 0/10 |
| Buffer Control | S. boydii 2 | 8/10 |
| Enteroinvasive E. coli O152 Invaplex 24 | E. coli O152 | 0/10[4] |
| Enteroinvasive E. coli O152 Invaplex 50 | E. coli O152 | 0/10[4] |
| Buffer Control | E. coli O152 | 6/10[4] |

[1]Guinea pigs were immunized intranasally 3 times with 25 ug of the Invaplex preparation per dose. The animals were immunized on days 0, 14, and 28 and challenged on day 49.
[2]Animals were infected with 3–6 × 10^8 cfu of the challenge agent which was the same strain used to prepare the Invaplex vaccine.
[3]Animals were considered to be positive for disease if they had a 2+ or 3+ rating (severe keratoconjunctivitis with purulence or keratoconjunctivitis without purulence) based on the scale developed by Hartman et al. (IAI 59:4075, 1991). The "# positive/total" refers to the number of eyes with disease over total number of eyes challenged.
[4]Control animals infected with enteroinvasive E. coli did not have severe (3+) disease levels. Immunized animals did not show any signs of disease.

EXAMPLE 4
Dose Response Experiments with The Invaplex 24 and Invaplex 50 Vaccines.

Figure 4:
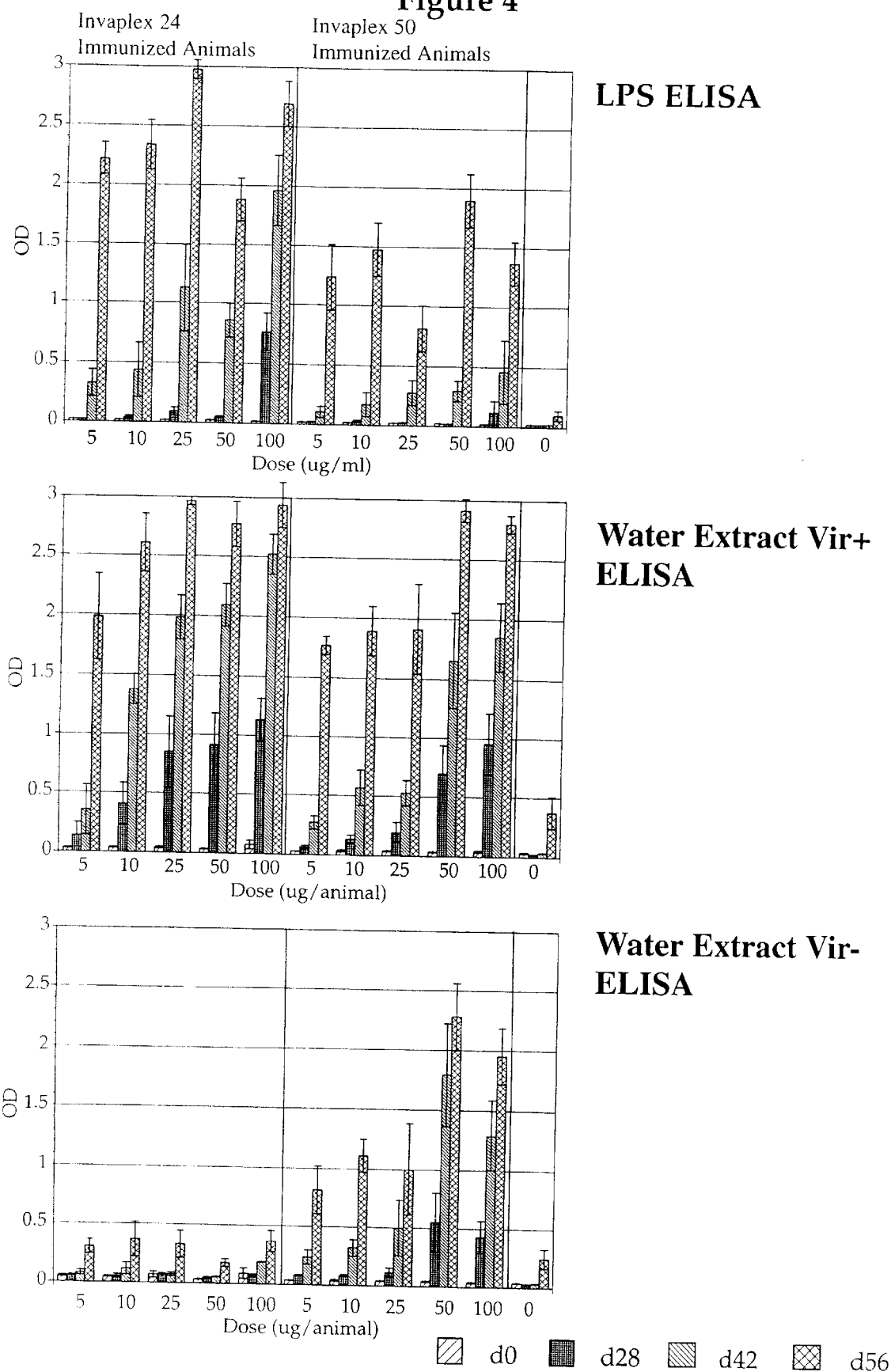
FIG. 4. Antibody response to LPS and water extract in guinea pigs immunized with different doses of Invaplex 24 or Invaplex 50 vaccine and subsequently challenged with virulent *S. flexneri* 2a. Five groups of guinea pigs (4 animals per group) were immunized with either 0, 5, 10, 25, 50 or 100 ug/dose of *S. flexneri* 2a Invaplex 24 or Invaplex 50. Guinea pigs were immunized intranasally on days 0, 14, and 28 and then challenged on day 49. Blood was collected on days 0, 28, 42 and 56. The serum IgG response was measured by ELISA against *S. flexneri* 2a LPS (top panel), water extract from Vir+ (middle panel) and Vir− (bottom panel) shigellae. In each of the 3 panels, the Invaplex 24 immunized animal data are on the left, the Invaplex 50 immunized animal data are in the middle, and the buffer control animal data are on the right side of each graph. The bars represent the mean $O.D._{405}\pm S.E.M.$ for each group of 4 guinea pigs. The vaccine dosage (ug) is indicated below the data for each group of guinea pigs.

Experiments were conducted to determine the immunogenicity of the S. flexnei 2a Invaplex 24 and Invaplex 50 vaccines. Guinea pigs (4 per group) were immunized with either 0, 5, 10, 25, 50, or 100 ug of Invaplex per dose. Each animal was immunized intranasally 3 times at two week intervals. Several different ELISAs were used to measure the antibody response generated in response to the different doses of Invaplex (FIG. 4). Against LPS gradually higher levels of anti-LPS IgG were present with increasing doses of Invaplex (FIG. 4A). The Invaplex 24 vaccine produced somewhat higher anti-LPS levels than the Invaplex 50 vaccine. At the 10 ug dose, a positive anti-LPS response is present after two doses of vaccine. At lower doses a positive anti-LPS response isn't detectable until after three immunizations.

Higher levels of antibodies reactive with the water extract were evident in the animals receiving higher doses of Invaplex (FIG. 4 middle and bottom panel). However antibodies to the water extract antigen were detected in the lowest dose of (5 ug) group after 3 immunizations. Positive antibody responses against the vir+ water extract were evident in all dose groups for Invaplex 24 after just 2 doses, while for Invaplex 50 a positive antibody response after 2 doses was evident in animals immunized with 25 ug of Invaplex of above. As noted above, Invaplex 24, at all doses, produced a striking virulence specific antibody response, whereas Invaplex 50 produced antibodies reactive with both vir+ and vir– water extract antigens. The Invaplex 50 response occurred at all doses.

The potent immune response in guinea pigs immunized with 5 to 100 ug of either Invaplex 24 or Invaplex 50 was sufficient to protect guinea pigs upon challenge with virulent S. flexneri 2a in the Sereny test. The level of protection was at least 80% for each group as compared to saline buffer control animals in which all animals developed disease (0% protection).

EXAMPLE 5
Safety and Side-Effects of the Invaplex 24 and Invaplex 50.

Animals (guinea pigs or mice) intranasally immunized with Invaplex 24 or Invaplex 50 showed no visible side effects (fur ruffling, lethargy, diarrhea) after immunization. In mice this lack of toxicity was observed at doses of 5 and 10 ug and for guinea pigs the lack of toxicity was evident for doses ranging from 5 ug up to 100 ug. In addition guinea pigs immunized with either Invaplex 24 or Invaplex 50 gained weight at a comparable rate to guinea pigs treated with normal saline. This indicates that water intake and food intake was normal for these animals. Weight gain was not measured in mice but there was no apparent lack of weight gain in mice immunized with the Invaplex 24 or Invaplex 50 preparations.

EXAMPLE 6
Further purification of Invaplex 24 and Invaplex 50 by Gel Filtration Chromatography.

Gel filtration chromatography was used to further purify the Invaplex collected from ion-exchange chromatography fractions. Invaplex samples were applied to a Superose 6 HR10/30 column (Pharmacia, Uppsala, Sweden) equilibrated with 20 mM Tris-HCl (pH 9) containing 0.24M NaCl (for Invaplex 24 separations) or 0.5 M NaCl (for Invaplex 50 separations). Fractions (0.5 ml) were collected and analyzed for the presence of IpaB, IpaC, and LPS using immuno spot-blots, western blots, or silver stained polyacrylamide gels. The column was standardized with proteins of known molecular weights.

For Invaplex 24, a large complex (greater than 670,000 mw) containing LPS, IpaB and IpaC was found. The fractions containing this large molecular weight complex were separated from smaller sized protein-containing fractions. For Invaplex 50, a large complex (greater than 670,000 mw) containing LPS, IpaB and IpaC was also found. The fractions containing this large molecular weight complex were separated from smaller sized protein-containing fractions.

DISCUSSION

Shigellosis is a leading cause of human diarrheal disease. Each year millions of cases occur particularly in developing countries and it is estimated that over 1 million cases result in death (Kotloff et al, 1999, Bull. WHO 77, 651–666). The constant emergence of antibiotic resistance in Shigella, even to the newest antibiotics, underscores the need for an effective vaccine to help control Shigella disease. Unfortunately, vaccine strategies must consider the need for protection against 4 species of Shigella (S. flexneri, S. sonnei, S. dysenteriae, and S. boydii) as well as enteroinvasive E. coli as cross-protection is not significant. Compounding this problem is the fact that there are over 45 different serotypes and the level of protective cross-reactions between these serotypes is not known. Present vaccine strategies include living attenuated vaccines (Coster, et al., 1999, *Infect. Immun.* 67, 3437–3443) and also delivery of Shigella LPS or O-polysaccharides with carriers such as proteosomes (Orr et al., 1993, *Infect. Immun.* 61, 2390–2395) or protein carriers such as tetanus toxoid (Polotsky, et al, 1994, *Infect. Immun.* 62, 210–214).

The protective immune response which is necessary to prevent future Shigella infections is not completely understood. In natural infections the immune system produces antibodies to LPS and to several virulence proteins, including IpaC, IpaB, and at lower frequency IpaD, IpaA and VirG. Recent studies have indicated that the Shigella virulence proteins or invasins actually are associated together in a complex, and it is hypothesized that this complex is the functional entity involved in the invasive event (Menard et al, 1996, *Proc. Natl. Acad. Sci. USA* 93, 1254–1258). It is not known if the invasin complex is recognized as an intact structure by the immune system but if it is then it is very likely that invasin-complex antibodies may occur. Such antibodies could have a role in neutralizing invasive shigellae.

Recent studies have indicated that the Shigella invasins, specifically IpaB and IpaC are associated together in spent culture medium and that this IpaB:IpaC complex may be involved in the interaction with host cell membranes leading to eventual phagocytosis of the bacterium (Menard et al., 1996, supra). It is not clear if the IpaB:IpaC complex found in culture medium is actually the active structure involved in the invasive event. It is more likely that the active complex resides on the surface of the shigellae and will be activated and released upon exposure to the proper stimulus such as close proximity of a host cell or detection of a host cell biochemical indicating a host cell is nearby. In this study a novel method has been developed for isolating a macromolecular structure containing the major known virulence factors and immunogens from intact, viable, virulent shigellae. This structure is called the invasin complex or "Invaplex" and it contains the invasins (Ipa proteins) and LPS. Two forms of the Invaplex have been isolated by FPLC ion-exchange chromatography. They are the Invaplex 24 and Invaplex 50 preparations. Both Invaplex 24 and Invaplex 50 contain IpaB, IpaC, IpaD, IpaA and LPS. VirG*, a truncated form of VirG, is found only in Invaplex 50. Invaplex 24 and Invaplex 50 have been isolated from all 4 species of Shigella and also EIEC. Invaplex 24 or Invaplex 50 derived from each species is similar with respect to Ipa protein content and LPS content. Run to run consistency is very high making the production of Invaplex a reproducible procedure.

The availability of a subunit preparation derived from shigellae which contains the major antigens and virulence factors provides a reagent that could be used for the measurement of the immune response to an intact virulence structure and also provides a novel subunit approach to Shigella vaccines.

Our studies indicate that both Invaplex 24 and Invaplex 50 are very immunogenic in mice and in guinea pigs. Intranasal immunizations, without any additional adjuvant, stimulated both an IgA and IgG response to LPS, and to antigens in the water extract ELISA antigen. This includes IpaC, IpaB and other virulence proteins. Interestingly, Invaplex 24 produced a virulent specific antibody response very similar to that produced in monkeys or humans infected with Shigella spp. (Oaks et al., 1986, *Infect. Immun.* 53, 57–63) Invaplex 50 stimulated a serum antibody response which was not virulent specific (as measured by the water extract ELISA). This indicates that non-plasmid encoded antigens are in the Invaplex 50 and are capable of stimulating an antibody response. Even so, Invaplex 50 preparations do stimulate antibodies to virulence proteins such as IpaC and IpaB, as determined by western blot analysis of immune sera.

Invaplex preparations from all species of Shigella were capable of stimulating an antibody response to the homologous immunizing Invaplex as measured by ELISA. Animals immunized with Invaplex 24 always had higher antibody levels to the immunizing antigen (i.e., Invaplex 24) than to the analogous (i.e., same shigella serotype) Invaplex 50 antigen. In the reciprocal situation, Invaplex 50 animals had higher antibody levels against the immunizing Invaplex 50 antigen than to the analogous (i.e., same Shigella serotype) Invaplex 24 antigen. These results are good evidence that the Invaplex 24 and Invaplex 50 contain unique antigens or possibly present antigens in a unique way resulting in a dominant immune response against the immunizing Invaplex. The unique immune response elicited to the two Invaplex preparations may be in part to the presence of VirG* in only the Invaplex 50 preparations.

Potent immune responses were achieved with small quantities of Invaplex. In mice, 5 or 10 ug, and in guinea pig 25 ug were capable of producing measurable antibody levels after 3 intranasal immunizations. In dose response experiments using *S. flexneri* 2a Invaplex 24 and Invaplex 50, it was possible to stimulate a measurable antibody response to LPS, water extract, or Invaplex with three, 5 ug dose of vaccine.

Higher doses (25, 50 and 100 ug) generated a positive antibody response after 2 intranasal doses. In all cases, animals immunized with Invaplex 24 or Invaplex 50, showed a dramatic increase in antibody levels upon challenge with virulent shigellae of the identical serotype of Invaplex vaccine. This rapid boost in titer (post-challenge blood was collected one week after challenge) is a result of the effective priming of the immune system by the Invaplex vaccines.

Delivering vaccines by the mucosal route (intranasal, oral, etc) is difficult and not very effective unless suitable mucosal adjuvants are used. The potent immune response generated by the Invaplex preparations and the known capacity of the Ipa proteins to interact with host cells suggest that the Invaplex might be able to enhance the immune response to co-administered antigens, somewhat like cholera toxin. The best mucosal adjuvant is cholera toxin in that it enhances a pronounced IgA response in secretions and blood as well as a serum IgG response. It has been established in mice, that the underlying immune mechanism stimulated by cholera toxin adjuvanticity is based on a T helper 2 (Th2) response This is characterized by increased levels of cytokines IL4 and IL5 which are released by activated T cells. This leads to increased levels of secretory and serum IgA. One effect of IL4 is that it promotes an IgG1 response (in mice) to the immunizing antigen. For example in mice immunized with a CT/ovalbumin mixture, the predominant immunoglobulin G subclass is IgG1 with low levels of IgG2b also being made against ovalbumin (Marinaro et al, 1995, supra). IgG2a and IgG3 are not stimulated by CT/ovalbumin after intranasal immunization. To determine the adjuvanticity of Invaplex 24 and Invaplex 50 mixtures of ovalbumin and Invaplex were administered intranasally to mice. Our results indicate that both Invaplex 24 and Invaplex 50 behave as adjuvants in that they enhanced the immune response to an otherwise non-immunogenic substance (i.e., ovalbumin). The antibody response to ovalbumin generated by ovalbumin/Invaplex mixtures was comparable to ovalbumin mixed with CT, a known mucosal adjuvant. Furthermore IgG subclass analysis of the anti-ovalbumin IgG response showed that the predominant IgG subclass generated was IgG1 which is indicative of a Th2 response. The IgG subclass response elicited by Invaplex/ovalbumin mixtures was almost identical to that produced in response to CT/ovalbumin mixtures. Additional characteristics of Th2 responses is increased IgA levels (Marinaro et al, 1995, supra) as a result of increased levels of IL-5. IgA levels were prominant in Invaplex immunized animals and furthermore Invaplex immunized animals are protected from challenge in the keratoconjunctivitis assay which is a mucosal challenge.

What is claimed is:

1. A vaccine for providing immune protection against infection with gram negative bacteria, said vaccine comprising an isolated lipopolysaccharide-protein complex isolated from a water extract of said gram-negative bacteria in an amount effective to elicit protective antibodies in a subject to said gram-negative bacteria and a pharmaceutically acceptable carrier, wherein the complex is in its native conformation and composed of at least one invasin protein associated with LPS of said gram-negative bacteria.

2. The vaccine according to claim 1 wherein said gram-negative bacteria is selected from the group consisting of Shigella, Escherichia, Salmonella, Yersinia, Rickettsia, Brucella, Erhlichiae, Edwardsiella, Campylobacter, Legionella and Neisseria.

3. The vaccine according to claim 1 wherein the vaccine is in a form suitable for administration by a route selected from the group consisting of oral, genital, subcutaneous, intradermal, intramuscular, intranasal, and transdermal.

4. A pharmaceutical composition comprising at least one isolated lipopolysaccharide-invasin protein complex in its native conformation isolated from a water extract of a gram-negative bacteria and a pharmaceutically acceptable excipient.

5. The composition of claim 4 wherein said composition further comprises a heterologous antigen.

6. The vaccine according to claim 1, comprising a dose containing 1 ng. to 10 mg. of said isolated lipopolysaccharide-invasin protein complex.

7. The vaccine of claim 1, comprising a dose containing from 100 ng. to 500 ug of said isolated lipopolysaccharide-invasin protein complex.

8. A kit comprising a vaccine according to claim 1 in a container with printed instructions on or accompanying the container concerning the administration of the composition to a patient to protect against or treat conditions caused by a gram-negative bacterial infection.

9. A method comprising administering to a subject a vaccine comprising a pharmaceutically acceptable excipient and an effective immunizing amount of isolated lipopolysaccharide-invasin protein complex isolated from a water extract in its native conformation, for prophylactic or therapeutic use in generating an immune response in a subject with a gram-negative bacterial infection.

* * * * *